(12) United States Patent
Nicholas et al.

(10) Patent No.: US 11,272,948 B2
(45) Date of Patent: Mar. 15, 2022

(54) HAND-HELD SURGICAL INSTRUMENTS

(71) Applicant: Covidien LP, Mansfield, MA (US)

(72) Inventors: David Nicholas, Trumbull, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 125 days.

(21) Appl. No.: 16/441,750

(22) Filed: Jun. 14, 2019

(65) Prior Publication Data

US 2020/0015836 A1 Jan. 16, 2020

Related U.S. Application Data

(60) Provisional application No. 62/695,883, filed on Jul. 10, 2018.

(51) Int. Cl.
  *A61B 17/29* (2006.01)
  *A61B 17/068* (2006.01)
  *A61B 17/00* (2006.01)

(52) U.S. Cl.
  CPC ........ *A61B 17/2909* (2013.01); *A61B 17/068* (2013.01); *A61B 2017/00017* (2013.01);
  (Continued)

(58) Field of Classification Search
  CPC ................ A61B 17/105; A61B 17/068; A61B 17/07207; A61B 90/90; A61B 90/98; A61B 2017/07278; A61B 2017/07285; A61B 2017/00398; A61B 2017/00473; A61B 2017/00477; A61B 2017/00951; A61B 2017/07271; A61B 2017/2927; A61B 2090/038; A61B 2090/0808; A61B 2017/00982; A61B 2017/00017; A61B 17/1155; A61B 2562/0261; A61B 2017/00526; A61B 90/03; A61B 34/30; A61B 50/13; A61B 50/33; A61B 90/92;
  (Continued)

(56) References Cited

U.S. PATENT DOCUMENTS 4,196,348 A 4/1980 Iwakiri et al.
4,803,362 A 2/1989 Butts
(Continued)

FOREIGN PATENT DOCUMENTS

CN 101227187 A 7/2008
CN 203014768 U 6/2013
(Continued)

OTHER PUBLICATIONS

European Search Report dated Feb. 3, 2020, corresponding to counterpart European Application No. 19185132.8; 15 pages.
(Continued)

*Primary Examiner* — Robert F Long (57) ABSTRACT

A hand-held surgical instrument includes a handle housing, a first motor disposed within the handle housing, a shaft portion extending distally from the handle housing, an articulation shaft operably coupled to the first motor and disposed within the shaft portion, and a position sensor associated with the articulation shaft. The articulation shaft is configured to axially move within the shaft portion to articulate an end effector, and the position sensor is configured to determine an articulation position of the articulation shaft.

17 Claims, 8 Drawing Sheets

(52) U.S. Cl.
CPC ............... *A61B 2017/0046* (2013.01); *A61B 2017/00398* (2013.01); *A61B 2017/00477* (2013.01); *A61B 2017/00734* (2013.01)

(58) Field of Classification Search
CPC ...... A61B 2090/0803; A61B 2090/031; A61B 2018/0063; A61B 2018/00988; A61B 18/1445; A61B 2018/1455; A61B 2017/00725; A61B 17/29; A61B 2017/00836; A61B 2017/00734; A61B 2017/00115; A61B 2017/07257; A61B 2017/00039; A61B 2017/00862
USPC ............................................ 227/175.1–182.1
See application file for complete search history.

(56) References Cited

U.S. PATENT DOCUMENTS

| | | | |
|---|---|---|---|
| 5,321,311 A | 6/1994 | Umemura et al. | |
| 5,508,686 A * | 4/1996 | Nihei | B25J 9/101 340/679 |
| 5,747,953 A | 5/1998 | Philipp | |
| 6,013,991 A | 1/2000 | Philipp | |
| 6,025,683 A | 2/2000 | Philipp | |
| 6,517,565 B1 | 2/2003 | Whitman et al. | |
| 6,960,894 B2 | 11/2005 | Carusillo et al. | |
| 7,638,958 B2 | 12/2009 | Philipp et al. | |
| 7,914,543 B2 * | 3/2011 | Roth | A61B 17/07207 606/153 |
| 8,480,703 B2 | 7/2013 | Nicholas et al. | |
| 8,968,276 B2 | 3/2015 | Zemlok et al. | |
| 9,283,054 B2 * | 3/2016 | Morgan | A61B 90/03 |
| 9,307,986 B2 | 4/2016 | Hall et al. | |
| 9,326,767 B2 | 5/2016 | Koch, Jr. et al. | |
| 9,358,003 B2 | 6/2016 | Hall et al. | |
| 9,398,911 B2 | 7/2016 | Auld | |
| 9,468,438 B2 | 10/2016 | Baber et al. | |
| 9,554,794 B2 | 1/2017 | Baber | |
| 9,597,104 B2 | 3/2017 | Nicholas et al. | |
| 9,654,050 B2 | 5/2017 | Kokinelis | |
| 9,700,309 B2 | 7/2017 | Jaworek | |
| 9,700,318 B2 | 7/2017 | Scirica et al. | |
| 9,775,610 B2 | 10/2017 | Nicholas et al. | |
| 9,782,169 B2 | 10/2017 | Kimsey | |
| 9,782,187 B2 | 10/2017 | Zergiebel | |
| 9,801,646 B2 | 10/2017 | Zergiebel | |
| 9,991,069 B2 | 6/2018 | Nicholas et al. | |
| 2008/0027279 A1* | 1/2008 | Abou El Kheir | A61B 1/05 600/111 |
| 2009/0090763 A1* | 4/2009 | Zemlok | A61B 90/98 227/175.2 |
| 2009/0095790 A1 | 4/2009 | Whitman et al. | |
| 2009/0108048 A1* | 4/2009 | Zemlok | A61B 17/00234 227/175.1 |
| 2009/0248041 A1* | 10/2009 | Williams | A61B 8/4488 606/130 |
| 2009/0283568 A1* | 11/2009 | Racenet | A61B 17/07207 227/181.1 |
| 2009/0314821 A1* | 12/2009 | Racenet | A61B 17/068 227/180.1 |
| 2010/0171026 A1 | 7/2010 | Saitou et al. | |
| 2010/0213240 A1* | 8/2010 | Kostrzewski | A61B 17/3209 227/180.1 |
| 2011/0017801 A1* | 1/2011 | Zemlok | A61B 17/07207 227/175.1 |
| 2011/0121049 A1 | 5/2011 | Malinouskas et al. | |
| 2011/0204119 A1 | 8/2011 | McCuen | |
| 2011/0295269 A1* | 12/2011 | Swensgard | A61B 34/71 606/130 |
| 2011/0295270 A1* | 12/2011 | Giordano | A61B 17/00234 606/130 |
| 2012/0012638 A1* | 1/2012 | Huang | A61B 17/115 227/176.1 |
| 2012/0089131 A1 | 4/2012 | Zemlok et al. | |
| 2012/0130420 A1 | 5/2012 | Nicholas | |
| 2012/0138660 A1* | 6/2012 | Shelton, IV | A61B 34/71 227/176.1 |
| 2012/0253329 A1 | 10/2012 | Zemlok et al. | |
| 2012/0296159 A1 | 11/2012 | Kanazawa et al. | |
| 2012/0296316 A1 | 11/2012 | Imuta | |
| 2012/0303002 A1* | 11/2012 | Chowaniec | A61B 17/07207 606/1 |
| 2013/0184730 A1 | 7/2013 | Beardsley et al. | |
| 2013/0319706 A1 | 12/2013 | Nicholas et al. | |
| 2013/0324979 A1 | 12/2013 | Nicholas et al. | |
| 2014/0012238 A1 | 1/2014 | Chen et al. | |
| 2014/0114403 A1 | 4/2014 | Dale et al. | |
| 2014/0246477 A1 | 9/2014 | Koch, Jr. et al. | |
| 2014/0246479 A1 | 9/2014 | Baber et al. | |
| 2014/0249557 A1 | 9/2014 | Koch, Jr. et al. | |
| 2014/0299647 A1 | 10/2014 | Scirica et al. | |
| 2014/0303668 A1 | 10/2014 | Nicholas et al. | |
| 2014/0305987 A1* | 10/2014 | Parihar | A61B 17/282 227/175.2 |
| 2014/0358129 A1 | 12/2014 | Zergiebel et al. | |
| 2015/0005788 A1* | 1/2015 | Sniffin | A61B 17/068 606/139 |
| 2015/0122870 A1* | 5/2015 | Zemlok | H02P 7/29 227/176.1 |
| 2015/0235789 A1 | 8/2015 | Calderoni | |
| 2015/0374372 A1 | 12/2015 | Zergiebel et al. | |
| 2016/0066916 A1* | 3/2016 | Overmyer | G06F 1/266 227/176.1 |
| 2016/0100838 A1* | 4/2016 | Beaupre | F16D 41/16 227/175.1 |
| 2016/0296268 A1* | 10/2016 | Gee | A61B 18/085 |
| 2016/0324514 A1* | 11/2016 | Srinivas | A61B 17/07207 |
| 2017/0202591 A1* | 7/2017 | Shelton, IV | A61B 18/00 |
| 2017/0224333 A1* | 8/2017 | Hunter | A61B 17/072 |
| 2017/0245854 A1 | 8/2017 | Zemlok et al. | |
| 2019/0000475 A1* | 1/2019 | Shelton, IV | A61B 17/07207 |
| 2019/0201034 A1* | 7/2019 | Shelton, IV | A61B 18/00 |
| 2019/0261984 A1* | 8/2019 | Nelson | A61B 17/07207 |

FOREIGN PATENT DOCUMENTS

| | | | |
|---|---|---|---|
| EP | 2055243 A2 | 5/2009 | |
| EP | 2455007 A2 | 5/2012 | |
| EP | 2777539 A2 | 9/2014 | |
| EP | 3011910 A1 | 4/2016 | |
| KR | 20020020332 A | 3/2002 | |
| KR | 20070000199 U | 2/2007 | |
| WO | 2008147415 A1 | 12/2008 | |
| WO | 2017123837 A2 | 7/2017 | |

OTHER PUBLICATIONS

European Search Report dated Oct. 23, 2019, corresponding to counterpart European Application No. 19185132.8; 14 pages.

* cited by examiner

HAND-HELD SURGICAL INSTRUMENTS

CROSS-REFERENCE TO RELATED APPLICATIONS

This application claims the benefit of and priority to U.S. Provisional Patent Application No. 62/695,883 filed Jul. 10, 2018, the entire disclosure of which is incorporated by reference herein.

BACKGROUND

1. Technical Field

The present disclosure relates to surgical instruments. More specifically, the present disclosure relates to hand-held electromechanical surgical instruments that articulate, rotate, and actuate a variety of other functions of surgical attachments, such as, for example, end effectors.

2. Background of Related Art

A number of handle assembly manufacturers have developed product lines with proprietary drive systems for operating and/or manipulating electromechanical surgical instruments. In many instances the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

Handle assemblies include various switches used to actuate one or more functions of a surgical end effector. It is desirable for switches to be intuitive to operate, ergonomic in design, and capable of actuating a variety of independent functions of hand-held electromechanical surgical instruments.

SUMMARY

In one aspect of the present disclosure, a hand-held surgical instrument is provided and includes a handle housing, a first motor disposed within the handle housing, a shaft portion extending distally from the handle housing, an articulation shaft, and a position sensor associated with the articulation shaft. The articulation shaft is operably coupled to the first motor and disposed within the shaft portion. The articulation shaft is configured to axially move within the shaft portion to articulate an end effector, and the position sensor is configured to determine an articulation position of the articulation shaft.

In aspects, the hand-held surgical instrument may further include a rack operably coupled between the articulation shaft and the position sensor. The rack may translate in response to axial movement of the articulation shaft to move the position sensor.

In other aspects, the rack may be arcuate and translate along an arcuate path in response to axial movement of the articulation shaft.

In some aspects, the position sensor may have a rotatable gear interfacing with the rack, such that translation of the rack rotates the rotatable gear.

In aspects, the position sensor may be a rotatory potentiometer.

In other aspects, the hand-held surgical instrument may further include an articulation block fixed with the articulation shaft and the rack. The articulation block may transfer the axial movement of the articulation shaft to the rack.

In some aspects, the hand-held surgical instrument may further include a drive nut operably coupled to the first motor and rotatable in response to an actuation of the first motor. The drive nut may be disposed about a proximal end portion of the articulation shaft and threadably coupled thereto, such that a rotation of the drive nut results in the axial movement of the articulation shaft.

In aspects, the position sensor may be a potentiometer, a capacitive sensor, a magnetoresistive sensor, an eddy-current sensor, a hall-effect sensor, or an optical sensor.

In other aspects, the hand-held surgical instrument may further include an articulation switch pivotably coupled to the handle housing and operably coupled to the first motor. An actuation of the articulation switch may activate the first motor.

In some aspects, the hand-held surgical instrument may further include a fire switch pivotably coupled to the handle portion at a location above the articulation switch. The fire switch may be configured to activate a clamping or firing of the end effector.

In aspects, the hand-held surgical instrument may further include a rotation switch rotationally coupled to the handle housing at a location proximally of the fire switch and above the articulation switch. The rotation switch may be configured to activate a rotation of the end effector.

In other aspects, the hand-held surgical instrument may further include a second motor operably coupled to the fire switch, and a third motor operably coupled to the rotation switch.

In some aspects, the hand-held surgical instrument may further include a printed circuit board disposed within the handle housing. The articulation switch, the fire switch, and the rotation switch may be in electrical communication with the printed circuit board.

In aspects, the hand-held surgical instrument may further include a pivot member keyed to the printed circuit board. The rotation switch may be rotationally coupled to the pivot member.

In a further aspect of the present disclosure, a handle assembly of a hand-held surgical instrument is provided and includes a handle housing, a first motor disposed within the handle housing, an articulation switch pivotably coupled to the handle housing, an articulation shaft operably coupled to the first motor, and a position sensor associated with the articulation shaft. The articulation switch is operably coupled to the first motor, such that an actuation of the articulation switch activates the first motor. The articulation shaft is configured to axially move in response to an actuation of the articulation switch, and the position sensor is configured to determine an articulation position of the articulation shaft.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical instruments including handle assemblies and switches thereof are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

As will be described in detail below, provided is a handle assembly of a hand-held surgical instrument having a plurality of switches for actuating a variety of functions of an end effector. One of the switches is an articulation switch operably coupled to an articulation shaft. The articulation shaft is configured to move axially to effect an articulation of the attached end effector in response to an activation of the articulation switch. The handle assembly includes a position sensor associated with the articulation shaft for monitoring an articulation orientation of the end effector based on an axial position of the articulation shaft. Further provided is an ergonomic handle housing having the switches arranged in a way that makes usage of the surgical instrument more intuitive for the clinician. Other features and benefits of the disclosed surgical instruments are further detailed below.

Figure 1:
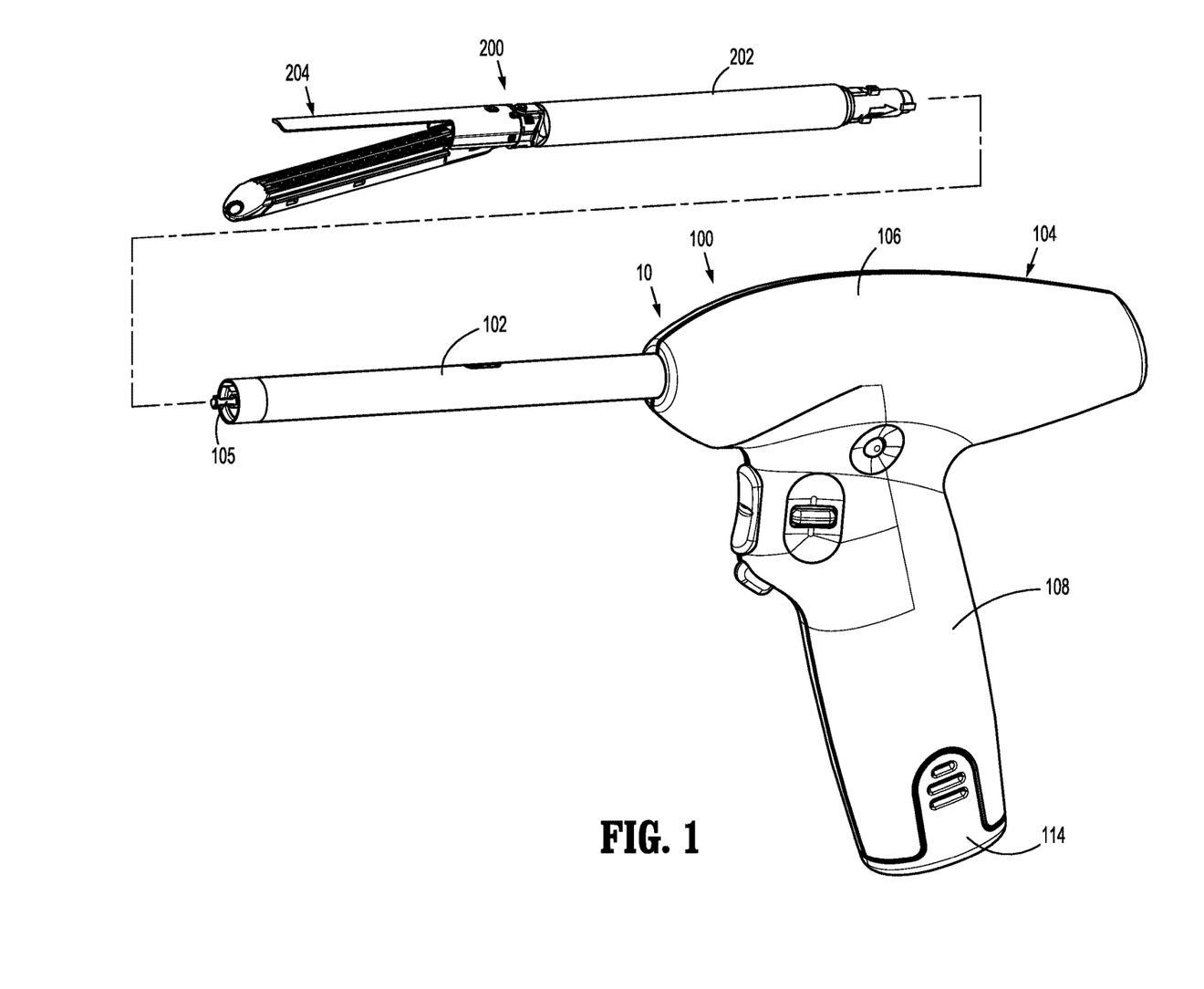
FIG. 1 is a perspective view of a hand-held electromechanical surgical instrument including a handle assembly, a shaft portion coupled to the handle assembly, and a surgical end effector separated from the shaft portion, in accordance with an embodiment of the present disclosure.
Figure 2:
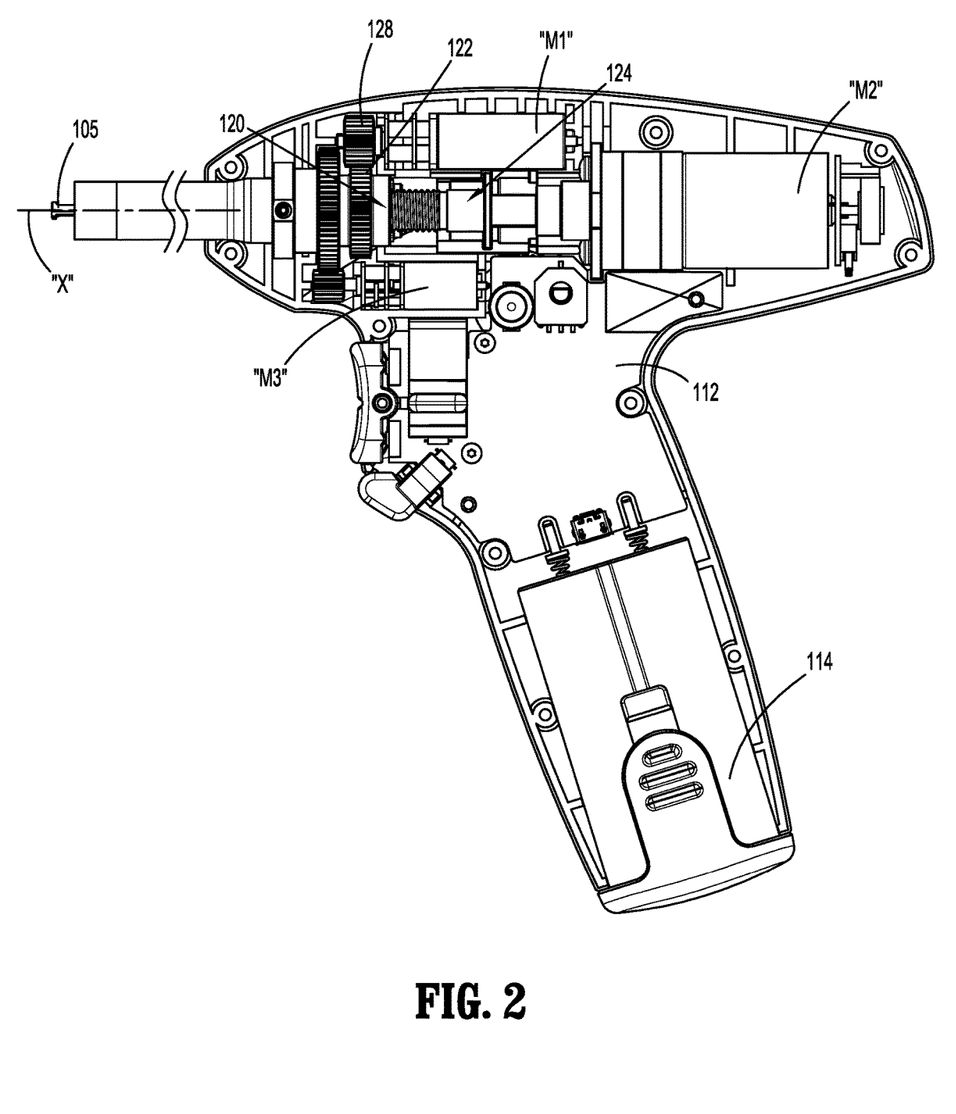
FIG. 2 is a side view, with a handle housing half removed, of the surgical instrument of FIG. 1.
Figure 3:
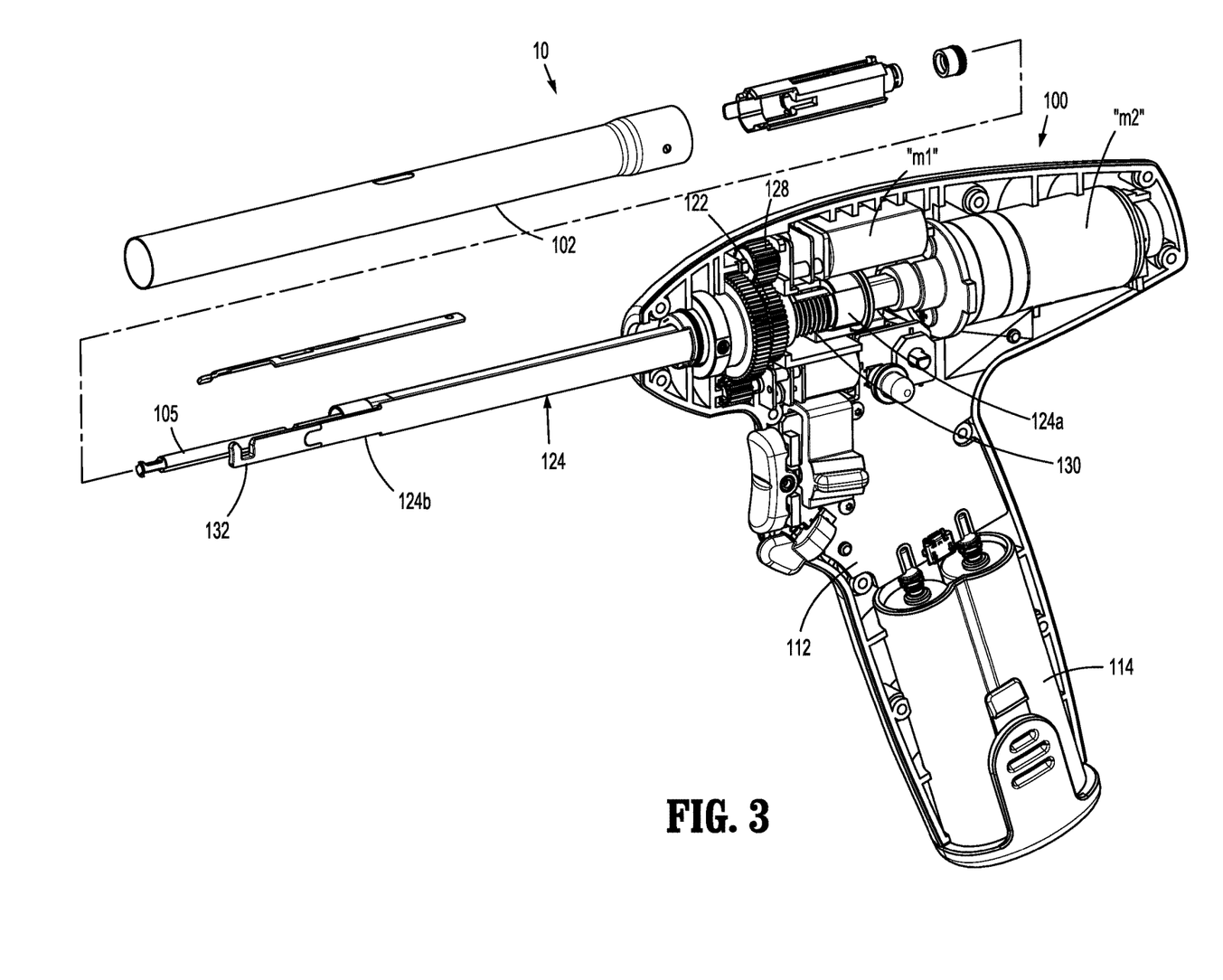
FIG. 3 is a side, perspective view, with parts separated, of the surgical instrument shown in FIG. 2.
Figure 4:
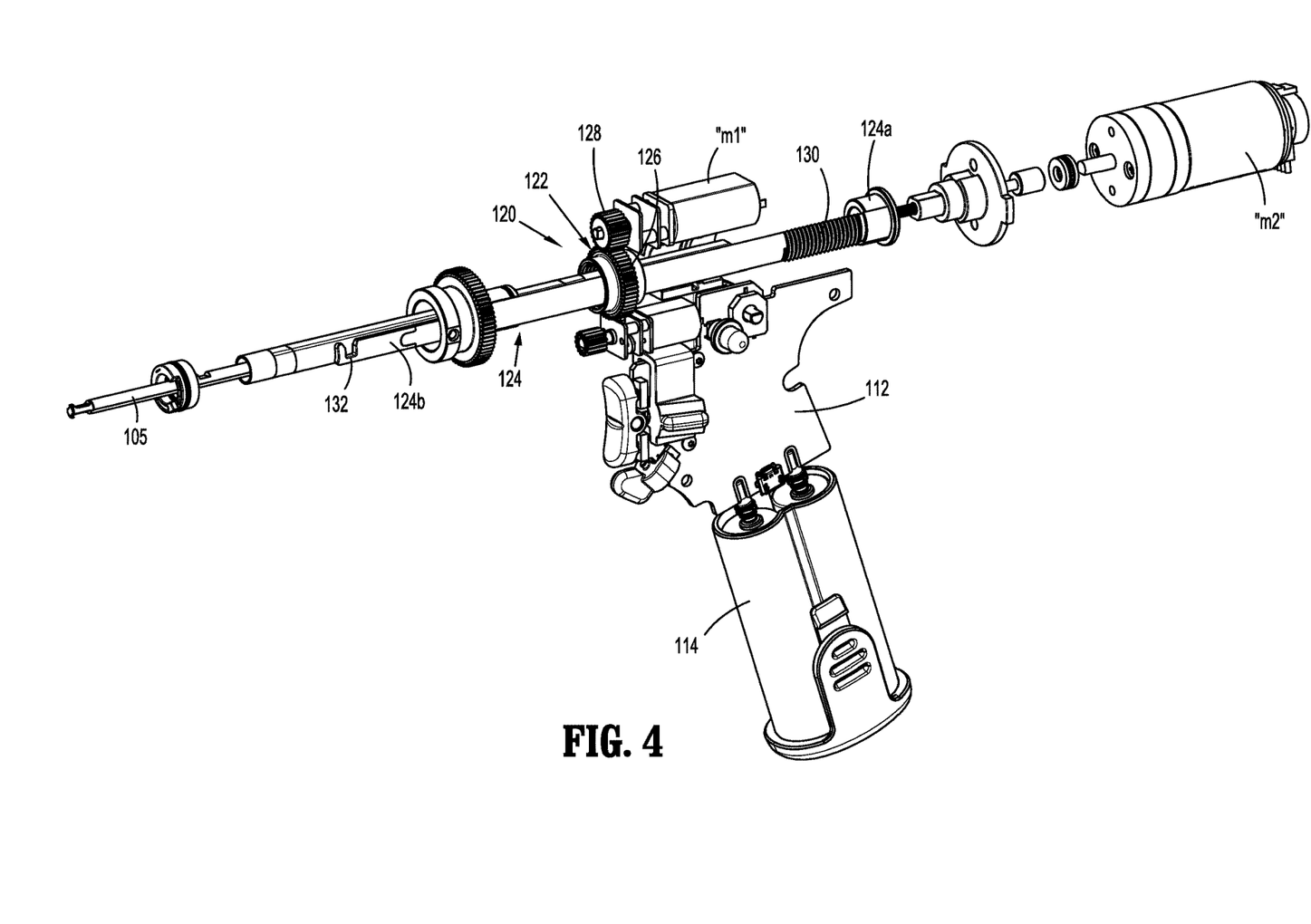
FIG. 4 is a side, perspective view of internal components of a handle assembly of the surgical instrument of FIG. 1.
Figure 10:
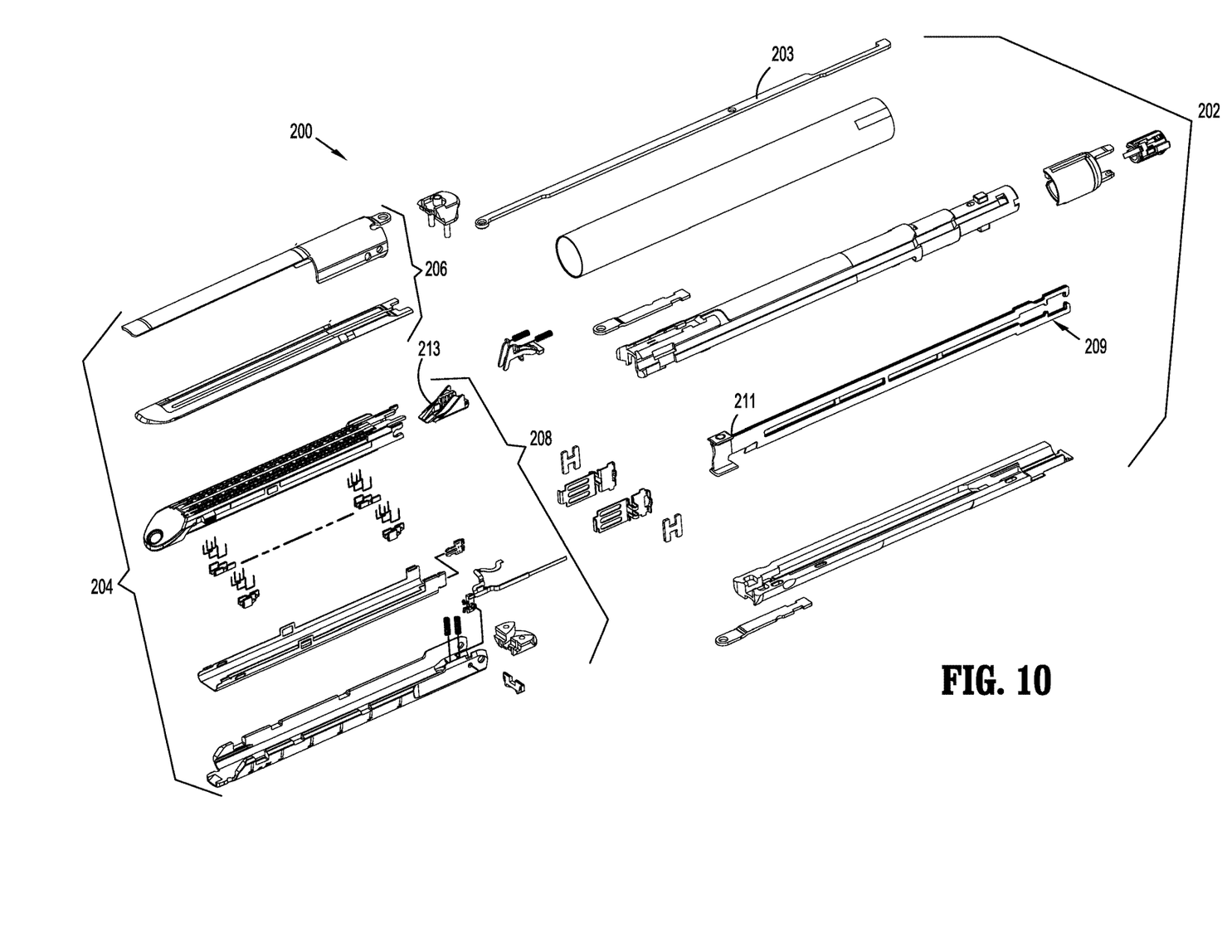
FIG. 10 is an exploded view of the surgical end effector of the hand-held electromechanical surgical instrument of FIG. 1.

With reference to FIGS. 1 and 2, a surgical instrument, in accordance with an embodiment of the present disclosure, is generally designated as 10, and is in the form of a powered hand-held electromechanical surgical instrument configured for selective coupling thereto of a plurality of different surgical end effectors, for example, the surgical end effector 200 of FIGS. 1 and 10. The end effector 200 is configured for actuation and manipulation by the powered hand-held electromechanical surgical instrument 10.

The hand-held electromechanical surgical instrument 10 includes a handle assembly 100 and a shaft portion 102 extending distally from the handle assembly 100 configured for selective connection with a surgical attachment, such as, for example, the end effector 200 (FIG. 10). The handle assembly 100 has a fire switch 162 configured and adapted to actuate the various functions of the end effector 200. In addition, the handle assembly 100 has an articulation switch 160 and a rotation switch 164 configured to respectively actuate an articulation of the end effector 200 (e.g., move the end effector 200 along a horizontal plane between a position coaxial with the shaft portion 102 and multiple positions out of alignment with the shaft portion 102) and rotate the end effector 200 (e.g., rotate the end effector 200 about a central longitudinal axis "X" defined by the shaft portion 102), as will be described in more detail herein.

The handle assembly 100 includes a handle housing 104 consisting of a body 106 and a handle portion 108 extending perpendicularly downward from the body 106. The body 106 of the handle housing 104 has a plurality of motors, for example, a first motor M1, a second motor M2, and a third motor M3, situated therein. The handle housing 104 further includes a motor controller printed circuit board 112 coupled to the plurality of motors M1-M3. The first motor M1, the second motor M2, and the third motor M3 are each electrically connected or wirelessly connected to the printed circuit board 112 and a battery pack 114 of the handle assembly 100. Each motor M1-M3 is controlled by a respective motor controller or processor (not explicitly shown). Rotation of motor shafts by respective motors M1-M3 function to drive shafts and/or gear components of the handle assembly 100 in order to perform the various operations of the end effector 200 (FIG. 10). For example, the first motor M1 is configured to articulate the end effector 200 relative to the shaft portion 102, the second motor M2 is configured to move jaw members 206, 208 (FIG. 10) of the end effector 200 relative to one another and/or to fire staples from the end effector 200, and the third motor M3 is configured to rotate the end effector 200 about the longitudinal axis "X" defined by the shaft portion 102.

With reference to FIGS. 2-7, the handle assembly 100 includes an articulation assembly 120 configured to effect the articulation of the end effector 200 (FIG. 10). The articulation assembly 120 has a drive nut 122 operably coupled to the first motor M1 and an articulation shaft 124 operably coupled to the drive nut 122. The drive nut 122 is axially restrained and rotatably supported in the body 106 of the handle housing 104. The drive nut 122 has a geared outer surface 126 and a threaded inner surface (not explicitly shown). The geared outer surface 126 of the drive nut 122 interfaces with a spur gear 128 fixed to a drive shaft of the first motor M1, such that rotation of the spur gear 128, via an activation of the first motor M1, causes the drive nut 122 to rotate. The drive nut 122 is disposed about a proximal end portion 124a of the articulation shaft 124, with the threaded inner surface of the drive nut 122 threadedly coupled to a threaded outer surface 130 of the proximal end portion 124a of the articulation shaft 124. As such, a rotation of the drive nut 122 drives the axial movement of the articulation shaft 124 in either a proximal or distal direction depending on the direction of rotation of the drive nut 122.

The articulation shaft 124 is laterally offset from the central longitudinal axis "X" defined by the shaft portion 102 and extends distally from within the handle housing 104 and through the shaft portion 102. The articulation shaft 124 has a distal end portion 124b defining a hooked feature 132 configured to interface with a proximal end of an articulation link 203 of the end effector 200 (FIG. 10) to drive the articulation of a tool assembly 204 of the end effector 200 relative to a proximal body portion 202 of the end effector 200. In embodiments, the distal end portion 124b of the articulation shaft 124 may have any suitable coupling arrangement with the end effector 200 to effect an articulation of the end effector 200, such as a rack and pinion connection, as shown and described in U.S. Patent Application Publication No. 2016/0324514, filed on May 6, 2015, the entire contents of which being incorporated by reference herein.

Figure 5:
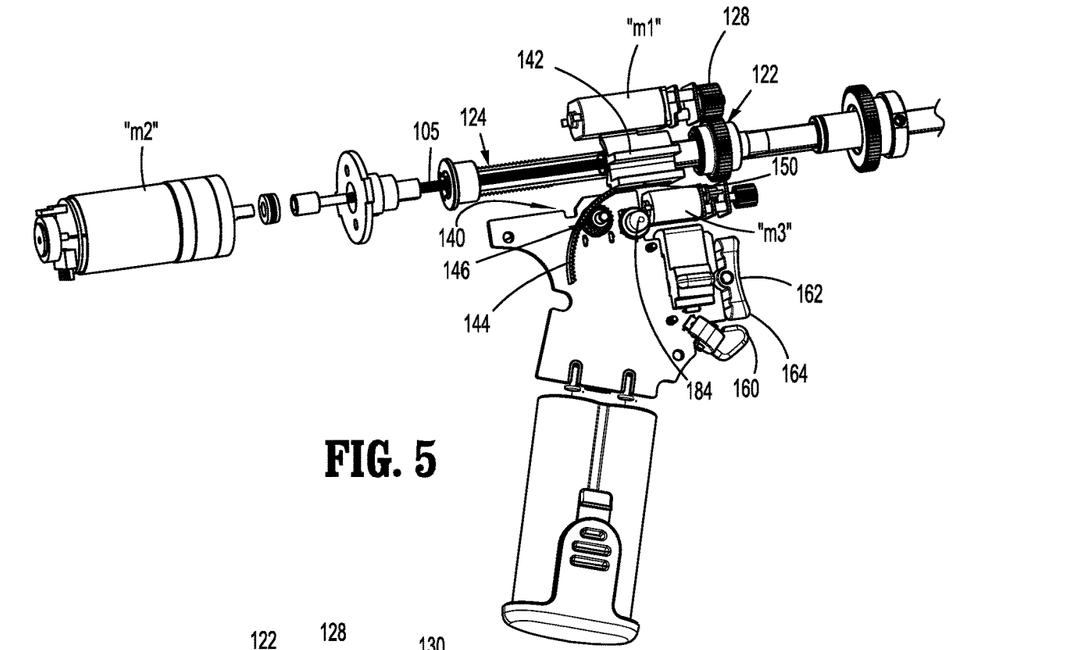
FIG. 5 is an alternate side, perspective view of the internal components of the handle assembly shown in FIG. 4.
Figure 6:
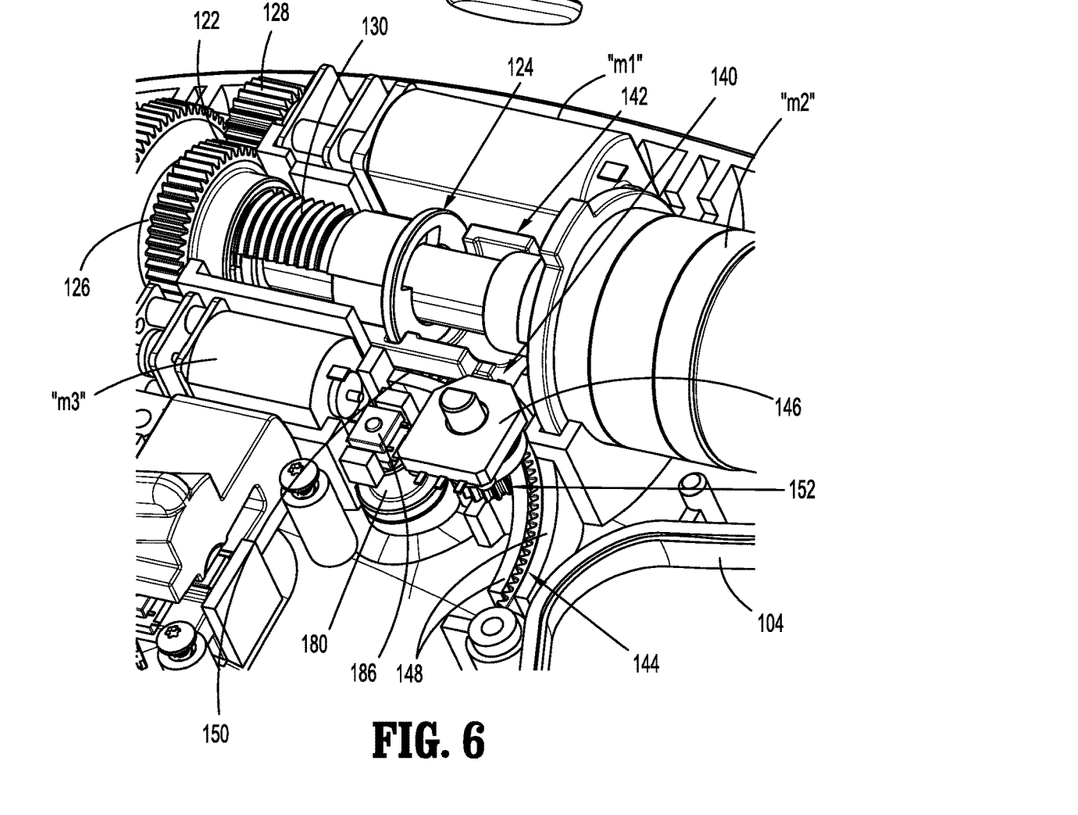
FIG. 6 is an enlarged perspective, side view of the internal components of the handle assembly shown in FIG. 5.
Figure 7:
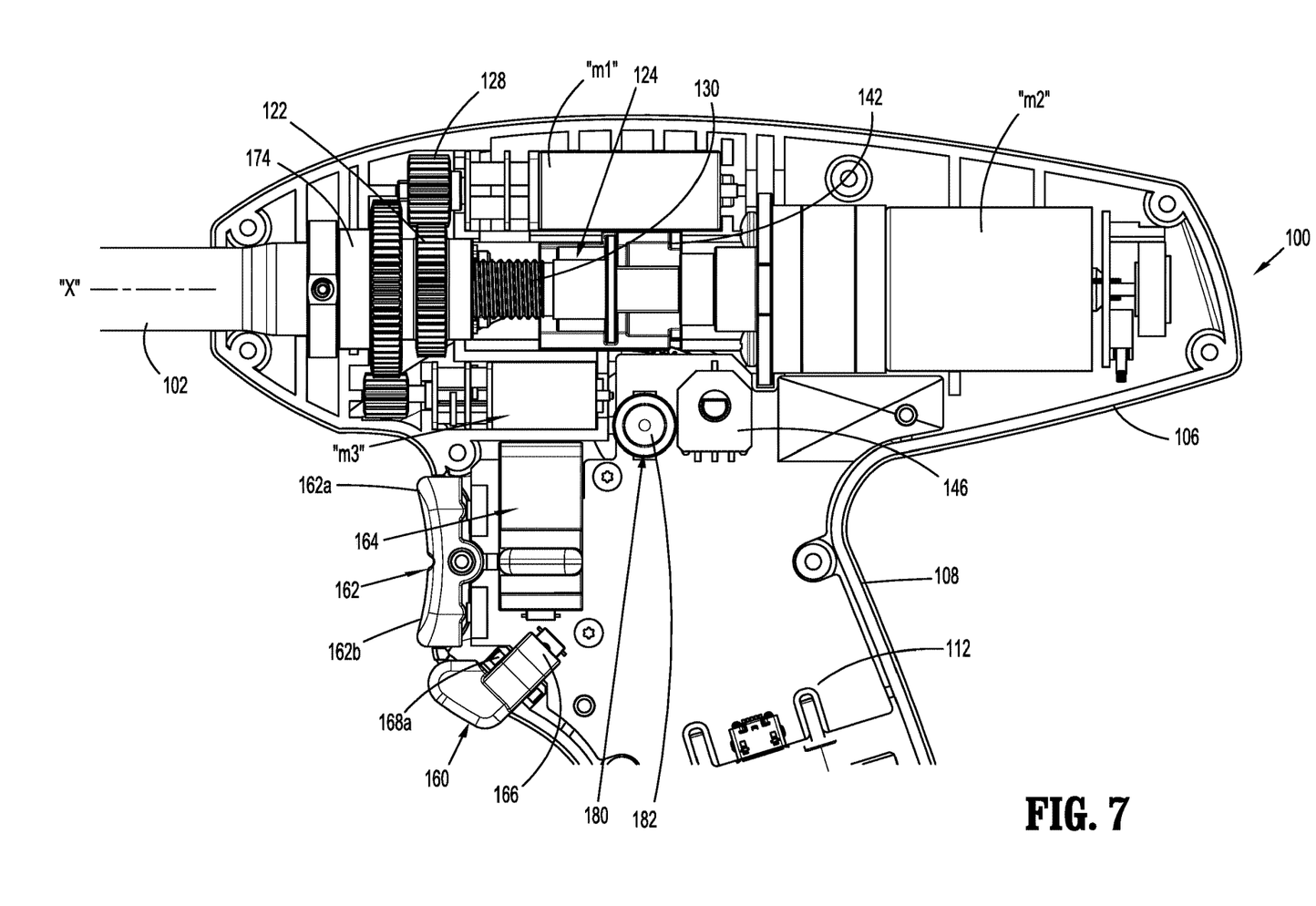
FIG. 7 is an enlarged side view, with a handle housing half removed, of the surgical instrument of FIG. 1.

As best shown in FIGS. 5-7, the handle assembly 100 further includes an articulation monitoring system 140 configured to sense the articulation position of the end effector 200 (FIG. 10) relative to the shaft portion 102. For example, the articulation monitoring system 140 may constantly determine the angle between a longitudinal axis defined by the end effector 200 and the longitudinal axis "X" defined by the shaft portion 102. The articulation monitoring system 140 includes an articulation block or slide 142, a rack 144, and a position sensor 146.

The articulation block 142 of the articulation monitoring system 140 is axially fixed with the proximal end portion 124a of the articulation shaft 124, whereby the articulation block 142 linearly translates with the articulation shaft 124. The rack 144 of the articulation monitoring system 140 may be flexible and have an arcuate shape. In embodiments, the rack 144 may assume any suitable shape, such as, for example, linear. The rack 144 is slidably disposed between a pair of guides 148 formed with the handle housing 104 to allow for translation of the rack 144 along an arcuate path. The rack 144 has a distal end portion 150 secured to the articulation block 142, such that linear movement of the articulation block 142 drives a translation of the rack 144 along the arcuate path. Gear teeth of the rack 144 interface with a spur gear 152 of the position sensor 146 to rotate the spur gear 152 of the position sensor 146 as the articulation shaft 124 moves axially.

The position sensor 146 is illustrated as a rotary potentiometer, however, it is contemplated that the position sensor 146 may be any suitable rotary or linear position sensor, such as, for example, a capacitive sensor, a magnetoresistive sensor, an eddy-current sensor, a hall-effect sensor, an optical sensor, or the like. The position sensor 146 is fixed within the handle housing 104 and is coupled to the rack 144. As the spur gear 152 of the position sensor 146 rotates, in response to movement of the rack 144, a sensed element in the position sensor 146, such as a wiper contact (not shown), moves relative to a sensing element in the position sensor 146, such as a resistive track (not shown), whereby the voltage between the wiper contact and the resistive track is monitored. The voltage determined by the position sensor 146 is proportional to the articulation angle of the end effector 200 (FIG. 10) relative to the shaft portion 102, thus providing the surgical instrument 10 with a means for detecting the articulation position of the end effector 200 at all times.

In operation, to articulate the end effector 200 relative to the shaft portion 102, the articulation switch 160 of the handle assembly 100 is actuated in either a left or right direction to articulate the end effector 200 in a corresponding direction. For example, moving the articulation switch 160 to the left may cause the printed circuit board 112 to transmit a signal to the first motor M1 to rotate its motor shaft and the attached spur gear 128 in a clockwise direction, thereby rotating the drive nut 122 of the articulation assembly 120 in a counter-clockwise direction. Since the drive nut 122 is threadedly coupled to the articulation shaft 124, the counter-clockwise rotation of the drive nut 122 drives a proximal movement of the articulation shaft 124 relative to and within the shaft portion 102 to articulate the end effector 200 to the left. Articulation of the end effector 200 towards the right may be accomplished by moving the articulation switch 160 to the right, which will set in motion the series of events described above, but in reverse.

In addition to effecting an articulation of the end effector 200, the proximal movement of the articulation shaft 124 retracts the articulation block 142 of the articulation monitoring system 140. As the articulation block 142 moves proximally, the rack 144 is translated along its arcuate pathway to rotate the spur gear 152 of the position sensor 146. Due to the amount of rotation of the spur gear 152 being commensurate with the amount of articulation of the end effector 200, the position sensor 146 accurately determines the amount the end effector has been articulated, giving the clinician, the surgical instrument 10, and/or an associated robotic system the articulation position of the end effector 200.

Figure 8:
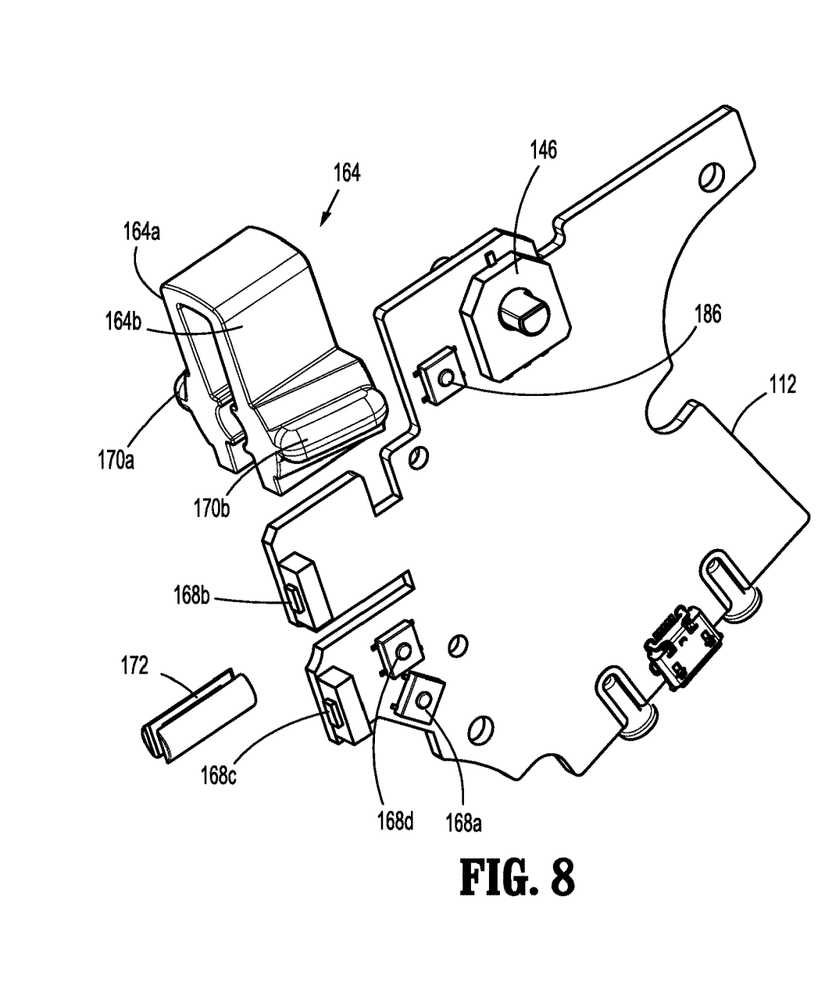
FIG. 8 is a side, perspective view of a rotation switch, a printed circuit board, and a pivot member of the handle assembly of FIG. 7 shown separated from one another.
Figure 9:
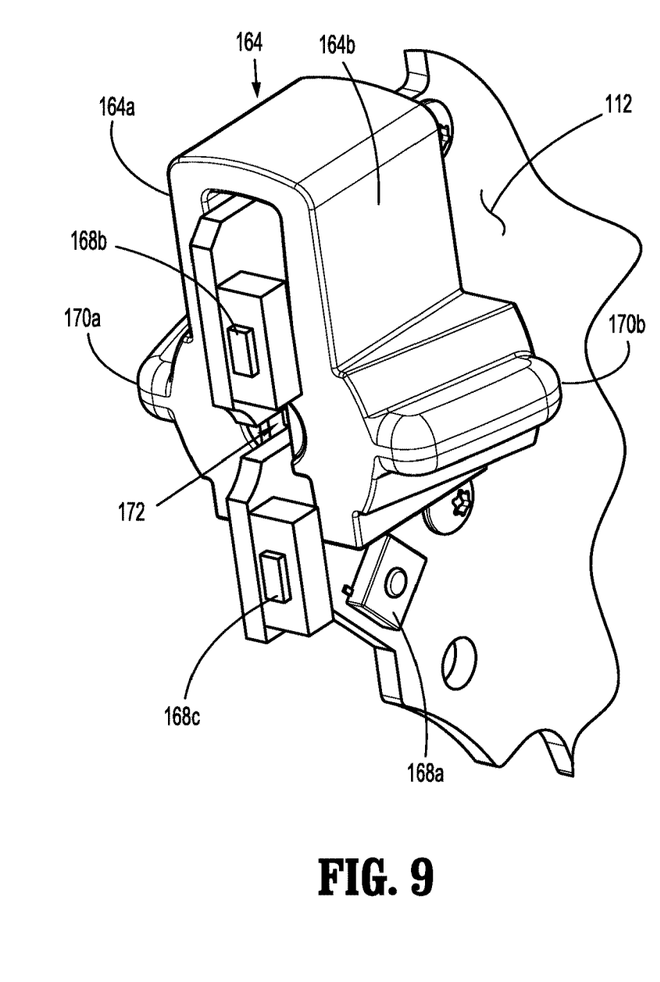
FIG. 9 is a side, perspective view of the rotation switch, the printed circuit board, and the pivot member of FIG. 8 shown assembled to one another.

With reference to FIGS. 7-9, the switches 160, 162, 164 of the handle assembly 100 will now be described in detail. The articulation switch 160 is swivelable relative to the handle portion 108 of the handle housing 104 in a left-right direction to ultimately effect an articulation of the end effector 200 (FIG. 10) in the corresponding direction, by way of the mechanical linkages described above. The articulation switch 160 has a bifurcated proximal end 166 that straddles opposing sides of the printed circuit board 112. The bifurcated proximal end 166 of the articulation switch 160 has a first finger that abuts a first contact switch 168a of the printed circuit board 112, and a second finger that abuts a second contact switch (not explicitly shown) of the printed circuit board 112. As such, swiveling the articulation switch 160 towards the left activates the first contact switch 168a, which activates the first motor M1 to articulate the end effector 200 towards the left, and swiveling the articulation switch 160 towards the right activates the second contact switch, which activates the first motor M1 to articulate the end effector 200 towards the right.

The fire switch 162 may be constructed as a toggle bar pivotably coupled to the handle portion 108 of the handle housing 104. The fire switch 162 extends perpendicularly relative to the longitudinal axis "X" of the shaft portion 102 and has a first end portion 162a and a second end portion 162b disposed on opposite sides of a pivot axis. The first end portion 162a abuts a third contact switch 168b of the printed circuit board 112, and the second end portion 162b abuts a fourth contact switch 168c of the printed circuit board 112. As such, an application of a proximally-oriented force on the first end portion 162a of the fire switch 162 pivots the fire switch 162 in a first direction to activate the third contact switch 168b, and an application of a proximally-oriented force on the second end portion 162b of the fire switch 162 pivots the fire switch 162 in a second direction to activate the fourth contact switch 168c. An activation of the third contact switch 168b activates the second motor M1 to advance a firing rod 105 of the surgical instrument 10. Since the firing rod 105 is coupled to a drive assembly 209 of the end effector 200 (which includes a knife rod 211 and an actuation sled 213, FIG. 10), advancement of the firing rod 105 advances the drive assembly 209 of the end effector 200, which both closes the jaw members 206, 208 of the end effector 200 and fires the end effector 200. An activation of the fourth contact switch 168c activates the second motor M1 to retract the firing rod 105, whereby the knife rod 211 of the drive assembly 209 of the end effector 200 retracts to open the jaw members 206, 208 of the end effector 200.

The rotation switch 164 is disposed proximally of (e.g., behind) the fire switch 162 and above the articulation switch 160 and is configured to rotate about a pivot axis parallel with the rotation axis of the end effector 200. The rotation switch 164 straddles the printed circuit board 112 and has a first lateral arm 164a exposed on a first lateral side of the handle portion 108 of the handle housing 104, and a second lateral arm 164b exposed on a second lateral side of the handle portion 108 of the handle housing 104. The first and second lateral arms 164a, 164b of the rotation switch 164 have a respective tab 170a, 170b positioned and configured for actuation by a finger of a clinician.

A pivot member 172, such as, for example, a pivot pin is keyed to the printed circuit board 112. The lateral arms 164a, 164b of the rotation switch 164 each define a rounded recess that together define a cylindrical passageway that accommodates the pivot member 172 therein. The lateral arms 164a, 164b of the rotation switch 164 are spaced from the respective opposing sides of the printed circuit board 112 to allow for rotation of the rotation switch 164 relative to and about the pivot member 172. The first lateral arm 164a of the rotation switch abuts a fifth contact switch (not explicitly shown) of the printed circuit board 112, and the second lateral arm 164b of the rotation switch 164 abuts a sixth contact switch 168d of the printed circuit board 112.

An application of an upwardly-oriented force on the first lateral arm 164a of the rotation switch 164 or a downwardly-oriented force on the second lateral arm 164b of the rotation switch 164 rotates the rotation switch 164 about the pivot member 172 in a first direction to activate the sixth contact switch 168d, and an application of an upwardly-oriented force on the second lateral arm 164b of the rotation switch 164 or a downwardly-oriented force on the first lateral arm 164a of the rotation switch 164 rotates the rotation switch 164 about the pivot member 172 in a second direction to activate the fifth contact switch. An activation of the sixth contact switch 168d activates the third motor M3 to rotate, in sequence, a spur gear 174, the shaft portion 102, and the attached end effector 200 about the longitudinal axis "X" of the shaft portion 102 in the first direction, and an activation of the fifth contact switch activates the third motor M3 to rotate, in sequence, the spur gear 174, the shaft portion 102, and the attached end effector 200 about the longitudinal axis "X" of the shaft portion 102 in the second direction.

As can be appreciated, a rotation of the shaft portion 102 may also cause the articulation shaft 124 to rotate relative to the drive nut 122, thereby inadvertently driving an articulation of the end effector 200. To counteract this, the processor may be configured to simultaneously activate the first motor M1 when the rotation switch 164 is actuated. In this way, the first motor M1 causes the drive nut 122 of the articulation assembly 120 to rotate in the same rotational direction as the shaft portion 102 to prevent relative rotation between the articulation shaft 124 and the drive nut 122. By the first motor M1 ensuring that the drive nut 122 rotates with the articulation shaft 124 about the longitudinal axis "X" of the shaft portion 102, unintentional articulation of the end effector 200 may be avoided.

In some embodiments, the switches 160, 162, 164 of the handle assembly 100 may be assigned to actuate various functions to be carried out by various surgical end effectors. It is contemplated that the switches 160, 162, 164 can be variously configured, such as, for example, as switches, rockers, flaps, latches, levers, dials, buttons, or touch screens.

With reference to FIGS. 5-9, the handle assembly 100 may further include a safety switch 180 constructed as an elongated bar extending transversely through the body 106 of the handle housing 104. The safety switch 180 has opposing end portions 182 (FIG. 7), 184 (FIG. 5) exposed from an outer surface of the handle housing 104 to allow a clinician to slide the safety switch 180 between a firing-disabled position and a firing-enabled position. In the firing-disabled position, the safety switch 180 one of contacts or disengages a contact switch 186 on the printed circuit board 112, whereby the processor is signaled to prevent an activation of the second motor M2 notwithstanding an actuation of the fire switch 162. In the firing-enabled position, the safety switch 180 contacts or disengages the contact switch 186, whereby the processor is signaled to allow an activation of the second motor M2 upon actuating the fire switch 162. It is contemplated that the safety switch 180 may be illuminated when in the firing-enabled position to give a clinician a visual indication that the safety is off and the surgical instrument 10 is ready for firing.

As illustrated in FIGS. 1 and 10, the end effector 200 is configured to be coupled to a distal end of the shaft portion 102 of the surgical instrument 10. The end effector 200 includes a proximal body portion 202 and a tool assembly 204. The proximal body portion 202 is releasably attached to the distal end the handle portion 102 and the tool assembly 204 is pivotally attached to a distal end of the proximal body portion 202 of the end effector 200. The proximal body portion 202 is configured to articulate relative to the distal end of the shaft portion 102 via longitudinal translation of the articulation link 203, as described above. The tool assembly 204 includes an anvil assembly 206 and a cartridge assembly 208. The cartridge assembly 208 is pivotal in relation to the anvil assembly 206 and is movable between an open or unclamped position and a closed or clamped position for insertion through a cannula of a trocar.

For a detailed discussion of the construction and operation of the surgical end effector 200, as illustrated in FIGS. 1 and 10, reference may be made to U.S. Pat. No. 7,819,896, filed on Aug. 31, 2009, entitled "TOOL ASSEMBLY FOR A SURGICAL STAPLING DEVICE," the entire contents of which being incorporated by reference herein.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments including switch assemblies. Therefore, the above description should not be construed as limiting, but merely as exemplifications of embodiments. Those skilled in the art will envision other modifications within the scope and spirit of the present disclosure.

What is claimed is:

1. A hand-held surgical instrument, comprising:
a handle housing;
a first motor disposed within the handle housing;
a shaft portion extending distally from the handle housing;
an articulation shaft operably coupled to the first motor and disposed within the shaft portion, the articulation shaft configured to axially move within the shaft portion to articulate an end effector;
a position sensor associated with the articulation shaft, wherein the position sensor is configured to determine an articulation position of the articulation shaft;
a rack operably coupled between the articulation shaft and the position sensor, wherein the rack translates in response to axial movement of the articulation shaft to move the position sensor, wherein the position sensor has a rotatable gear interfacing with the rack, such that translation of the rack rotates the rotatable gear; and a drive nut operably coupled to the first motor and rotatable in response to an actuation of the first motor, the articulation shaft having a proximal end portion received within and threadedly coupled to a threaded inner surface of the drive nut, such that a rotation of the drive nut results in the axial movement of the articulation shaft, wherein the drive nut is coaxial with the shaft portion, wherein the rack is arcuate and translates along an arcuate path in response to axial movement of the articulation shaft.

2. The hand-held surgical instrument according to claim 1, further comprising an articulation block fixed with the articulation shaft and the rack, wherein the articulation block transfers the axial movement of the articulation shaft to the rack.

3. The hand-held surgical instrument according to claim 1, further comprising an articulation switch operably coupled to the first motor, wherein an actuation of the articulation switch activates the first motor.

4. The hand-held surgical instrument according to claim 3, further comprising a fire switch pivotably coupled to the handle portion at a location above the articulation switch, wherein the fire switch is configured to activate a clamping or firing of the end effector.

5. The hand-held surgical instrument according to claim 4, further comprising a rotation switch rotationally coupled to the handle housing at a location proximally of the fire switch and above the articulation switch, wherein the rotation switch is configured to activate a rotation of the end effector.

6. The hand-held surgical instrument according to claim 5, further comprising:
a second motor operably coupled to the fire switch; and
a third motor operably coupled to the rotation switch.

7. The hand-held surgical instrument according to claim 5, further comprising a printed circuit board disposed within the handle housing, wherein the articulation switch, the fire switch, and the rotation switch are in electrical communication with the printed circuit board.

8. The hand-held surgical instrument according to claim 7, further comprising a pivot member keyed to the printed circuit board, the rotation switch being rotationally coupled to the pivot member.

9. A handle assembly of a hand-held surgical instrument, comprising:
a handle housing;
a first motor disposed within the handle housing;
an articulation switch operably coupled to the first motor, such that an actuation of the articulation switch activates the first motor;
an articulation shaft operably coupled to the first motor and configured to axially move in response to an actuation of the articulation switch;
a position sensor associated with the articulation shaft, wherein the position sensor is configured to determine an articulation position of the articulation shaft; and
a rack operably coupled between the articulation shaft and the position sensor, wherein the rack translates in response to axial movement of the articulation shaft to move the position sensor, wherein the position sensor has a rotatable gear interfacing with the rack, such that translation of the rack rotates the rotatable gear, wherein the rack is arcuate and translates along an arcuate path in response to axial movement of the articulation shaft.

10. The handle assembly according to claim 9, further comprising an articulation block fixed with the articulation shaft and the rack, wherein the articulation block transfers the axial movement of the articulation shaft to the rack.

11. The hand-held surgical instrument according to claim 1, wherein the proximal end portion of the articulation shaft is arcuate.

12. The handle assembly according to claim 9, further comprising a drive nut operably coupled to the first motor and rotatable in response to an actuation of the first motor, wherein the articulation shaft has a proximal end portion received within and threadedly coupled to a threaded inner surface of the drive nut, such that a rotation of the drive nut results in the axial movement of the articulation shaft.

13. A hand-held surgical instrument, comprising:
a handle housing;
a first motor disposed within the handle housing;
a shaft portion extending distally from the handle housing;
an articulation shaft operably coupled to the first motor and disposed within the shaft portion, the articulation shaft configured to axially move within the shaft portion to articulate an end effector;
a position sensor associated with the articulation shaft, wherein the position sensor is configured to determine an articulation position of the articulation shaft;
a rack operably coupled between the articulation shaft and the position sensor, wherein the rack translates in response to axial movement of the articulation shaft to move the position sensor, wherein the position sensor has a rotatable gear interfacing with the rack, such that translation of the rack rotates the rotatable gear;
a drive nut operably coupled to the first motor and rotatable in response to an actuation of the first motor, the articulation shaft having a proximal end portion received within and threadedly coupled to a threaded inner surface of the drive nut, such that a rotation of the drive nut results in the axial movement of the articulation shaft, wherein the drive nut is coaxial with the shaft portion;
an articulation switch operably coupled to the first motor, wherein an actuation of the articulation switch activates the first motor;
a fire switch pivotably coupled to the handle portion at a location above the articulation switch, wherein the fire switch is configured to activate a clamping or firing of the end effector;
a rotation switch rotationally coupled to the handle housing at a location proximally of the fire switch and above the articulation switch, wherein the rotation switch is configured to activate a rotation of the end effector;
a second motor operably coupled to the fire switch; and
a third motor operably coupled to the rotation switch.

14. The hand-held surgical instrument according to claim 13, further comprising a printed circuit board disposed within the handle housing, wherein the articulation switch, the fire switch, and the rotation switch are in electrical communication with the printed circuit board.

15. The hand-held surgical instrument according to claim 14, further comprising a pivot member keyed to the printed circuit board, the rotation switch being rotationally coupled to the pivot member.

16. The hand-held surgical instrument according to claim 13, further comprising an articulation block fixed with the articulation shaft and the rack, wherein the articulation block transfers the axial movement of the articulation shaft to the rack.

17. The hand-held surgical instrument according to claim 13, wherein the proximal end portion of the articulation shaft is arcuate.

\* \* \* \* \*